(12) United States Patent
Stein et al.

(10) Patent No.: US 11,766,248 B2
(45) Date of Patent: Sep. 26, 2023

(54) SYSTEM AND METHOD FOR DETERMINING TEMPERATURE NADIR OF A FEMALE

(71) Applicant: AVA AG, Zürich (CH)

(72) Inventors: Peter Stein, Zürich (CH); Brigitte Leeners, Uster (CH)

(73) Assignee: AVA AG, Zürich (CH)

( * ) Notice: Subject to any disclaimer, the term of this patent is extended or adjusted under 35 U.S.C. 154(b) by 0 days.

(21) Appl. No.: 16/320,936

(22) PCT Filed: Jul. 5, 2017

(86) PCT No.: PCT/EP2017/025197
§ 371 (c)(1),
(2) Date: Jan. 25, 2019

(87) PCT Pub. No.: WO2018/019431
PCT Pub. Date: Feb. 1, 2018

(65) Prior Publication Data
US 2019/0167237 A1    Jun. 6, 2019

(30) Foreign Application Priority Data

Jul. 28, 2016  (CH) .................................. 00987/16

(51) Int. Cl.
*A61B 10/00*     (2006.01)
*A61B 5/0205*    (2006.01)
(Continued)

(52) U.S. Cl.
CPC ............ *A61B 10/0012* (2013.01); *A61B 5/01* (2013.01); *A61B 5/02055* (2013.01);
(Continued)

(58) Field of Classification Search
CPC combination set(s) only.
See application file for complete search history.

(56) References Cited

U.S. PATENT DOCUMENTS

| 4,151,831 A | 5/1979 | Lester |
| 2013/0137940 A1 | 5/2013 | Schafer |

(Continued)

FOREIGN PATENT DOCUMENTS

WO    WO 2016102971 A2    6/2016

OTHER PUBLICATIONS

International Search Report and Written Opinion of the International Searching Authority issued in International Application No. PCT/EP2017/025197, dated Oct. 18, 2017, in 10 pages.

*Primary Examiner* — Scott Luan
(74) *Attorney, Agent, or Firm* — Knobbe, Martens, Olson & Bear, LLP (57) ABSTRACT

An electronic system for determining a time of the temperature nadir of a female human during the menstrual cycle comprises a wearable device (1) that includes a first sensor system (104), configured to determine a temperature of the female human, and a second sensor system (101, 102, 103), configured to determine one or more further physiological parameters of the female human. The electronic system further comprises a processor (13, 30, 40), configured to determine a detected starting point of the fertility phase of the female human, using the one or more further physiological parameters of the female human. The processor (13, 30, 40) is further configured to detect the temperature nadir as a temporary decrease in the temperature, using the detected starting point of the fertility phase of the female human. The time of the temperature nadir is used as an indicator of the time of ovulation and peak oestrogen level.

16 Claims, 7 Drawing Sheets

(51) Int. Cl.
*A61B 5/01* (2006.01)
*A61B 5/024* (2006.01)
*A61B 5/00* (2006.01)
*A61B 5/0533* (2021.01)

(52) U.S. Cl.
CPC ........ *A61B 5/02438* (2013.01); *A61B 5/0533* (2013.01); *A61B 5/4306* (2013.01); *A61B 2010/0016* (2013.01); *A61B 2010/0019* (2013.01); *A61B 2010/0029* (2013.01)

(56) References Cited

U.S. PATENT DOCUMENTS

2017/0007214 A1* 1/2017 Dillen .................. A61B 5/0002
2019/0110692 A1* 4/2019 Pardey ................. A61B 5/7282

* cited by examiner

SYSTEM AND METHOD FOR DETERMINING TEMPERATURE NADIR OF A FEMALE

CROSS-REFERENCE TO RELATED APPLICATIONS

This application is the U.S. National Phase under 35 U.S.C. § 371 of International Application PCT/EP2017/025197, filed Jul. 5, 2017, which claims priority to CH Application No. 00987/16, filed Jul. 28, 2016.

FIELD OF THE INVENTION

The present invention relates to an electronic system and a method for determining a temperature nadir during a menstrual cycle of a female human. Specifically, the present invention relates to an electronic system and a method for determining a temperature nadir during a menstrual cycle of a female human using a wearable device with sensor systems for measuring physiological parameters.

BACKGROUND OF THE INVENTION

Since the introduction of the contraceptive pill in 1960, decades have passed without major developments in the birth control market. In the recent years, so called fertility apps for mobile devices were becoming attractive for an increasing number of women. These applications use the calendar method for determining fertile time periods. Nevertheless, most non-hormonal birth control tools, such as these apps or the well-known temperature method, are found cumbersome and unreliable by many women. Generally, by relying on more than one physiological parameter the reliability can be increased significantly for determining the fertility phase of a female in connection with non-hormonal birth control. For example, the so-called symptothermal method uses a combined analysis of cervical mucus and temperature measurements for determining the fertile and infertile days of a woman. While this yields a better reliability, it is typically found complicated and very cumbersome by women.

The fertile window consists of six consecutive days with ovulation at the last day. It is characterized by low conception probabilities during the first days and high conception probabilities at the end (Wilcox A J, Weinberg C R, Baird D D. Timing of Sexual Intercourse in Relation to Ovulation. *Obstet Gynecol Surv.* 1995). Especially, the hours around ovulation are highly fertile. Recognition of ovulation supports diagnostics and—in case of natural contraception—allows to determine the end of the fertile window (when sexual intercourse does not bear chances of conception anymore) as early as possible. But neither the classical temperature method nor the symptothermal method allow precise detection of ovulation in real-time. The most commonly used non-invasive indicator for ovulation is an increase in basal body temperature by approx. 0.4 C. As scientific studies have proven this increase in temperature occurs after ovulation (e.g. Ecochard R, Boehringer H, Rabilloud M, Marret H. Chronological aspects of ultrasonic, hormonal, and other indirect indices of ovulation. *Br J Obstet Gynaecol.* 2001) and can often just be detected 3 days after ovulation. A real-time indicator for ovulation is a basal body temperature minimum called the temperature nadir. This temperature minimum is induced by the highest level of estrogen during the menstrual cycle, which typically take place in the 24 hours before ovulation. Due to the fact that the temperature nadir is characterized by a decrease of approx. 0.1 C in the signal, and that signal noise from confounding parameters are in the same range, it is hardly possible to identify the correct temperature nadir.

WO 97/22298 describes an apparatus with a microprocessor that processes data from wrist worn sensors measuring eccrine sweat to observe the pattern in pH change during the menstrual cycle for determining the fertility status of a female.

CN 203314947U describes a multifunctional watch that comprises a microprocessor and a temperature sensor for monitoring the menstrual cycle of a female.

US 2004/081024 describes another wristwatch that comprises a temperature sensor and a computing device for predicting the ovulation phase.

US 2002/0156394 describes an apparatus which is inserted into the vagina of cattle for detecting estrus.

US 2014/246500 mentions that ovulation can be detected with wrist based collected data. US 2014/246500 does neither describe how to process the collected data, nor make it possible to predict ovulation and to determine in advance the fertile phase which would be valuable for women who want to become pregnant.

WO 2015/150434 describes an unobtrusive ovulation tracking system using a subject's heart rate. The time of ovulation is considered a particularly fertile time. According to WO 2015/150434, the likelihood of ovulation is predicted based on heart rate variability features extracted from the heart rate. While heart rate variability is useful as an indicator for ovulation, its reliability is affected by various external influences such as drugs, e.g. alcohol or caffeine, or stress, etc.

WO 2016/102971 describes a processing system for analysing data values obtained from a sensor which indicates the basal body temperature of a female user. A series of representative temperature values for 24 hour periods is stored. The system analyzes the series of representative temperature values to determine whether it includes a temperature change event that indicates ovulation. Specifically, an onset of phase change (OPC) from follicular phase to luteal phase is detected based on an increase of basal temperature. Ovulation is assumed typically three days after OPC and its actual occurrence is verified based on criteria related to sustained temperature increase, as indicated by moving averages of measured temperature values above defined thresholds. WO 2016/102971 does not rely on or refer to a temperature nadir.

US 2013/0137940 describes a temperature based fertility monitoring system based on temperature and electrical resistivity of the saliva and/or cervical fluid. US 2013/0137940 relies on a nadir of electrical resistivity measurements but does not rely on or refer to a temperature nadir.

SUMMARY OF THE INVENTION

It is an object of this invention to provide an electronic system and a method for determining the temperature nadir during a menstrual cycle of a female human, which system and method do not have at least some of the disadvantages of the prior art. In particular, it is an object of the present invention to provide an electronic system and a method for determining the temperature nadir during a menstrual cycle of a female human, which system and method do not rely primarily and/or solely on the heart rate.

According to the present invention, these objects are achieved through the features of the independent claims. In addition, further advantageous embodiments follow from the dependent claims and the description.

According to the present invention, the above-mentioned objects are particularly achieved in that an electronic system for determining a temperature nadir during a menstrual cycle of a female human comprises a wearable device that includes a first sensor system, configured to be worn in contact with the skin of the female human and to determine a temperature of the female human. The electronic system further comprises a processor configured to receive the temperature of the female human from the first sensor system and one or more further physiological parameters of the female human. The processor is further configured to determine a detected starting point of a fertility phase of the female human, using the one or more further physiological parameters of the female human. The processor is further configured to detect the temperature nadir as a temporary decrease in the temperature received from the first sensor system, using the detected starting point of the fertility phase of the female human, the time of the temperature nadir being indicative of time of ovulation and peak oestrogen level.

In an embodiment, the processor is configured to determine the nadir of the temperature by detecting the temporary decrease of the temperature within a time window around a probable time when the ovulation or peak oestrogen level is expected to occur. The probable time is determined by the processor based on the detected starting point of the fertility phase of the female human. Detecting the nadir as a temporary decrease of the temperature within a probable time window makes it possible to precisely identify the temperature nadir in real time.

In a further embodiment, the processor is configured to determine the probable time when the ovulation or peak oestrogen level is expected to occur as a first time-probability distribution, indicating for various points in time of the time window the probability of the ovulation or peak oestrogen level to occur, and to determine a second time-probability distribution, indicating for various points in time of the time window the probability of the nadir of the temperature to occur, by detecting the temporary decrease of the temperature, and to determine the time of the temperature nadir by comparing a combination of the first time-probability distribution and the second time-probability distribution to a threshold. Comparing combined time-probability distributions of ovulation and nadir to a threshold makes it possible to precisely identify the temperature nadir in real time as an indicator of the time of ovulation and peak oestrogen level.

In an embodiment, the processor is configured to determine the probable time when the ovulation or peak oestrogen level is expected to occur by adding a probable time duration to the detected starting point of the fertility phase.

In a further embodiment, the wearable device includes a second sensor system configured to be worn in contact with the skin of the female human and to determine a heart rate of the female human; and the processor is configured to determine a change in pulse during a menstrual cycle using the heart rate, and to determine the detected starting point of the fertility phase, using the change in the pulse.

In an embodiment, the processor is configured to determine the detected starting point of the fertility phase using the time of the change of the pulse from a comparatively short interval between heartbeats to a comparatively longer interval between heartbeats.

In a further embodiment, the processor is configured to determine the detected starting point of the fertility phase by detecting a time indicative of an end point of a period of pulses with a comparatively long interval between heartbeats.

In an embodiment, the wearable device includes a second sensor system configured to be worn in contact with the skin of the female human and to determine a heart rate variability of the female human; and the processor is configured to determine the detected starting point of the fertility phase, using a time of increased heart rate variability.

In a further embodiment, the second sensor system is configured to determine acceleration of the female human; and the processor is configured to detect during menstrual cycles sleep phases with resting pulse using the heart rate variability and the acceleration, to determine a change in the resting pulse during a menstrual cycle using the heart rate, and to determine the detected starting point of the fertility phase, using a time of the change in the resting pulse.

In an embodiment, the processor is configured to determine the detected starting point of the fertility phase using external indicators in addition to or instead of physiological parameters of the female human measured by sensor systems included in the wearable device. Such external indicators are physiological parameters of the female human, which obtained through measurements and/or devices separate from and external to the wearable device, e.g. results from a urine or saliva test, indicating the presence of an estrogen metabolite, which is indicative of a fertile phase.

In an embodiment, wearable device includes a second sensor system configured to be worn in contact with the skin of the female human and to determine one or more further physiological parameters of the female human, and the processor is configured to determine correlations of the one or more further physiological parameters measured by the second sensor system and/or of other external indicators related to the female human, and to determine the detected starting point of the fertility phase, using the (correlation) time of the correlations of the one or more further physiological parameters and other external indicators.

In a further embodiment, the electronic system further comprises a data store, and the processor is configured to store in the data store one or more further physiological parameters measured by a second sensor system, included in the wearable device and configured to be worn in contact with the skin of the female human, and/or other external indicators related to the female human, and to determine the probable time when the ovulation or peak oestrogen level is expected to occur, using the one or more further physiological parameters and other external indicators of the female human stored during a plurality of menstrual cycles.

In an embodiment, the processor is arranged in the wearable device and configured to determine the time of the temperature nadir using physiological parameters measured by the sensor systems of the wearable device.

In a further embodiment, the processor is arranged in an external system, separated from the wearable device, the wearable device further comprises a communication module configured to transmit physiological parameters measured by the sensor systems of the wearable device to the external system, and the processor is configured to determine the time of the temperature nadir using the physiological parameters received from the wearable device.

In addition to the electronic system, the present invention also relates to a method of determining a temperature nadir during a menstrual cycle of a female human. The method comprises receiving in a processor from a first sensor system of a wearable device a temperature of the female human; receiving in the processor one or more further physiological parameters of the female human; determining by the processor a detected starting point of a fertility phase of the female human, using the one or more further physiological parameters of the female human; and detecting by the processor the temperature nadir as a temporary decrease in the temperature, using the detected starting point ($t_f$) of the fertility phase (403) of the female human, the time of the temperature nadir being indicative of time of ovulation and peak oestrogen level.

In an embodiment, the method further comprises determining by the processor a probable time when the ovulation or peak oestrogen level is expected to occur as a first time-probability distribution, indicating for various points in time of the time window the probability of the ovulation or peak oestrogen level to occur; and determining by the processor a second time-probability distribution, indicating for various points in time of the time window the probability of the nadir of the temperature to occur, by detecting the temporary decrease of the temperature; and determining by the processor the time of the temperature nadir by comparing a combination of the first time-probability distribution and the second time-probability distribution to a threshold.

In addition to an electronic system and a method of determining temperature nadir during a menstrual cycle of a female human, the present invention also relates to a computer program product comprising a non-transient computer-readable medium having stored thereon computer program code configured to control one or more processors of a computerized system. The computer program code is configured to control the one or more processors such that the computerized system performs the steps of: receiving from a first sensor system of a wearable device a temperature of the female human; receiving one or more further physiological parameters of the female human; determining a detected starting point of a fertility phase of the female human, using the one or more further physiological parameters of the female human; detecting a temperature nadir as a temporary decrease in the temperature, using the detected starting point of the fertility phase of the female human, the time of the temperature nadir being indicative of time of ovulation and peak oestrogen level.

As outlined above, the temperature nadir is induced by the peak oestrogen level and constitutes a real-time indicator for ovulation; accordingly, the precise and real-time detection of the temperature nadir described above makes it further possible to detect the time of ovulation and of peak oestrogen level. Thus, the present invention also relates to an electronic system configured to determine the time of ovulation and/or peak oestrogen level of a female human and a method of determining the time of ovulation and/or peak oestrogen level of a female human. Specifically, the electronic system and the method are configured to determine the time of ovulation and/or peak oestrogen level of a female human by receiving in a processor from a first sensor system of a wearable device a temperature of the female human; receiving in the processor from a second sensor system of the wearable device or from another (external) system or method one or more further physiological parameters of the female human; determining by the processor the detected starting point of a fertility phase of the female human, as outlined above, using one or more further physiological parameters and/or external indicators of the female human; determining by the processor the temperature nadir as a temporary decrease in the temperature, as outlined above, using the detected starting point of the fertility phase of the female human, as outlined above; and using the time of the temperature nadir as the time of ovulation and/or peak oestrogen level of the female human.

BRIEF DESCRIPTION OF THE DRAWINGS

The present invention will be explained in more detail, by way of example, with reference to the drawings in which.

DETAILED DESCRIPTION OF THE PREFERRED EMBODIMENTS

Figure 1:
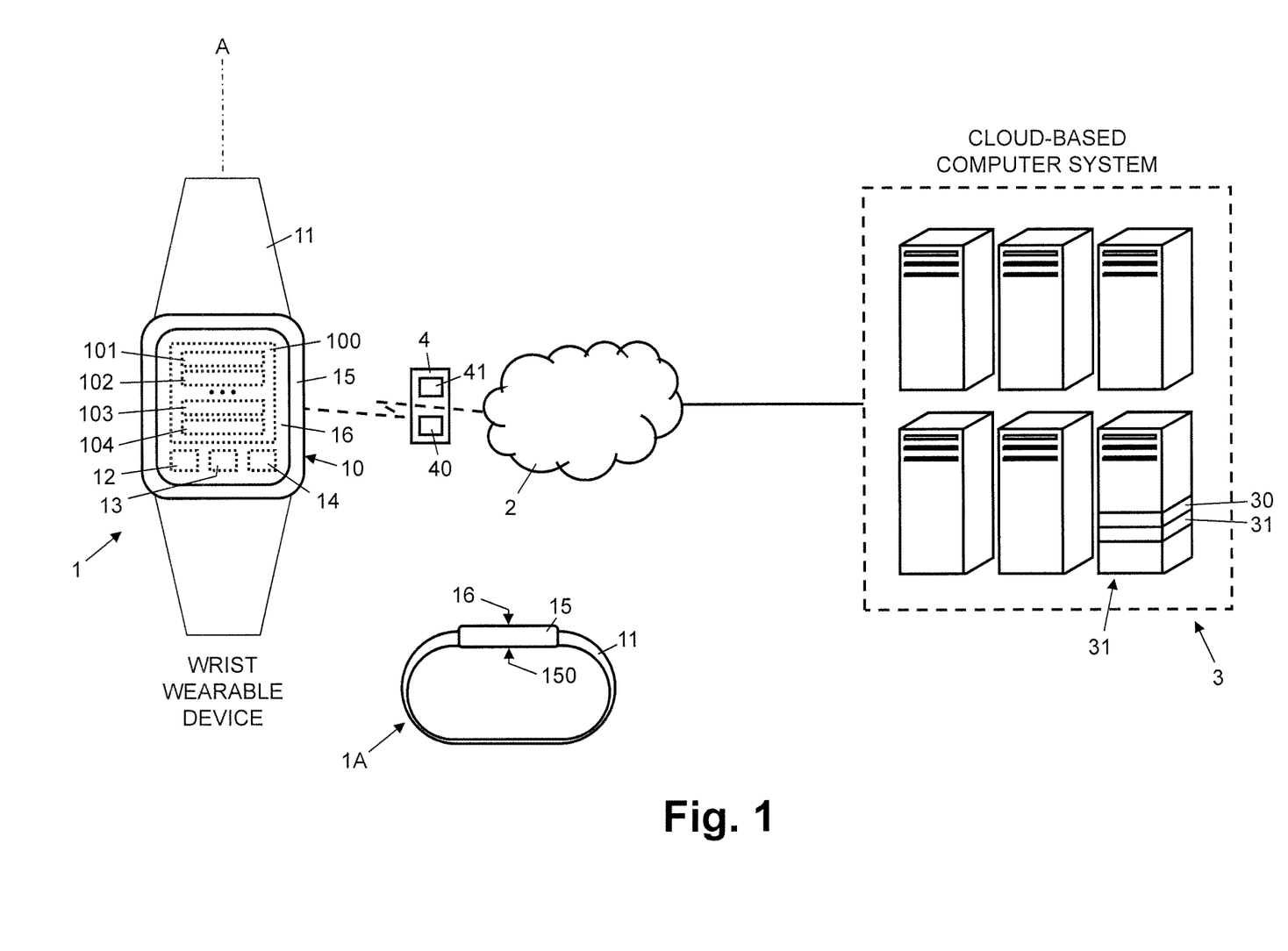
FIG. 1: shows a block diagram illustrating schematically an electronic system for determining and indicating the temperature nadir during a menstrual cycle of a female human, as an indicator for ovulation and peak oestrogen level of the female human, the system comprising a wearable device and a processor with a processor in the wearable device and/or an external system.

In FIG. 1, reference numeral 3 refers to a computer system, e.g. a cloud-based computer system, comprising one or more computers 31 with one or more processors 30 and a data storage system 31. The computer system 3 or its processors 30, respectively, are connected to the data storage system 31 and configured to execute various functions, as will be explained later in more detail. The data storage system 31 comprises RAM, flash memory, hard disks, data memory, and/or other data stores.

In FIG. 1, reference numeral 4 refers to a mobile communication device, e.g. a cellular telephone or a tablet computer, comprising one or more processors 40 and a data store 41. The processors 40 are connected to the data store and configured to execute various functions, as will be explained later in more detail. The data store comprises RAM, flash memory, data memory, and/or other data storage systems.

In FIG. 1, reference numeral 1 refers to a wearable device, e.g. a wrist wearable device, specifically a wrist wearable electronic device. Reference numeral 1A refers to a cross-sectional view of the wearable device 1 along central axis A. The wearable device 1 includes a fixation system for attaching the wearable device 1 on the body of a user, specifically, for attaching the wearable device 1 in contact with the skin of the user; in the embodiment shown in FIG. 1, the wearable device 1 comprises a wrist band 11 and a device body 10 attached to or integrated in the wrist band 11. The wristband 11 is implemented as a watchstrap, a watchband, a bracelet, or the like. The device body 10 comprises a housing 15 and an optional display 16 integrated in the housing 15. As illustrated schematically in FIG. 1, wearable device 1 comprises several sensor systems 100, including a sensor system 101 with optical sensors 101 configured to generate photoplethysmography (PPG) signals for measuring heart rate, heart rate variability, and perfusion. For example, sensor system 101 comprises a PPG-based sensor system for measuring heart rate and heart rate variability as described in Simon Arberet et al., "Photoplethysmography-Based Ambulatory Heartbeat Monitoring Embedded into a Dedicated Bracelet", Computing in Cardiology 2013; 40:935-938, included herewith by reference in its entirety. The sensor systems 100 further include a sensor system 102 with one or more accelerometers for measuring body movements (acceleration). In an embodiment, for the purpose of sleep phase analysis the accelerometers are implemented in combination with the PPG-based sensor system, as described in Philippe Renevey et al., "PHOTOPLETHYS-MOGRAPHY-BASED BRACELET FOR AUTOMATIC SLEEP STAGES CLASSIFICATION: PRELIMINARY RESULTS", IASTED 2014, Zurich, Switzerland, included herewith by reference in its entirety. The sensor systems 100 further include a temperature sensor system 104 for measuring the user's temperature; specifically, the user's skin temperature; more specifically, the wrist's skin temperature. The temperature sensor system 104 comprises one or more sensors, including at least one temperature sensor and in an embodiment one or more additional sensor(s) for measuring further parameters like perfusion, bio-impedance and/or heat loss for determining the user's temperature. Depending on the embodiment, the sensor systems 100 further include a galvanic skin response sensor system 103 with an electrical resistance or conductance measuring system. The optical sensors 101, the galvanic skin response sensor system 103, and the temperature sensor system 104 are integrated in the housing 15 of the wearable device 1 and are arranged on a rear side 150 of the wearable device 1, e.g. opposite of the optional display 16, facing the user's skin in a mounted state of the wearable device 1. In the mounted state when the device 1 is actually attached and worn, e.g. on the wrist, just as one would wear a watch, the rear side 150 of the wearable device 1 or the rear side 150 of its housing 15, respectively, is in contact with the skin, e.g. the skin of the wrist, i.e. the optical sensors 101, the galvanic skin response sensor system 103, and the temperature sensor system 104 touch the skin or at least face the skin, e.g. the skin of the wrist. The wearable device 1 further comprises a data store 12, e.g. data memory such as RAM or flush memory, and an operational processor 13 connected to the data store 12 and the sensor systems 100. The processor 13 comprises an electronic circuit configured to perform various functions that will be described later in more detail.

As illustrated in FIG. 1, in an embodiment, the wearable device 1 further comprises a communication module 14 connected to the processor 13. The communication module 14 is configured for data communication with an external system 3, 4, that is separated from the wearable device 1, i.e. a computerized system that is arranged in a different housing than the wearable device 1. Depending on the embodiment and/or configuration, the external system is a remote computer system 3 or a mobile communication device 4. Accordingly, the communication module 14 is configured for data communication with the remote computer system 3 via a network 2 and/or with the mobile communication device 4 via a close range communication interface. The network 2 comprises a mobile radio network such as a GSM-network (Global System for Mobile communication), a UMTS-network (Universal Mobile Telephone System), or another mobile radio telephone system, a wireless local area network (WLAN), and/or the Internet. For example, for close range communication, the communication module 14 comprises a Bluetooth communication module, e.g. a Low Energy Bluetooth module, or another close range communication module configured for direct data communication with the external mobile communication device 4. In an alternative embodiment, the mobile communication device 4 is configured to facilitate the data communication between the wearable device 1 and the remote computer system 3, e.g. by relaying the measurement data from the wearable device 1 via the network 2 to the remote computer system 3, for processing. Although not illustrated, the wearable device 1 further comprises a timer module configured to generate current time and date information, e.g. a clock circuit or a programmed timer module. The timer module is further configured to generate time stamps including the current time and date.

Figure 4:
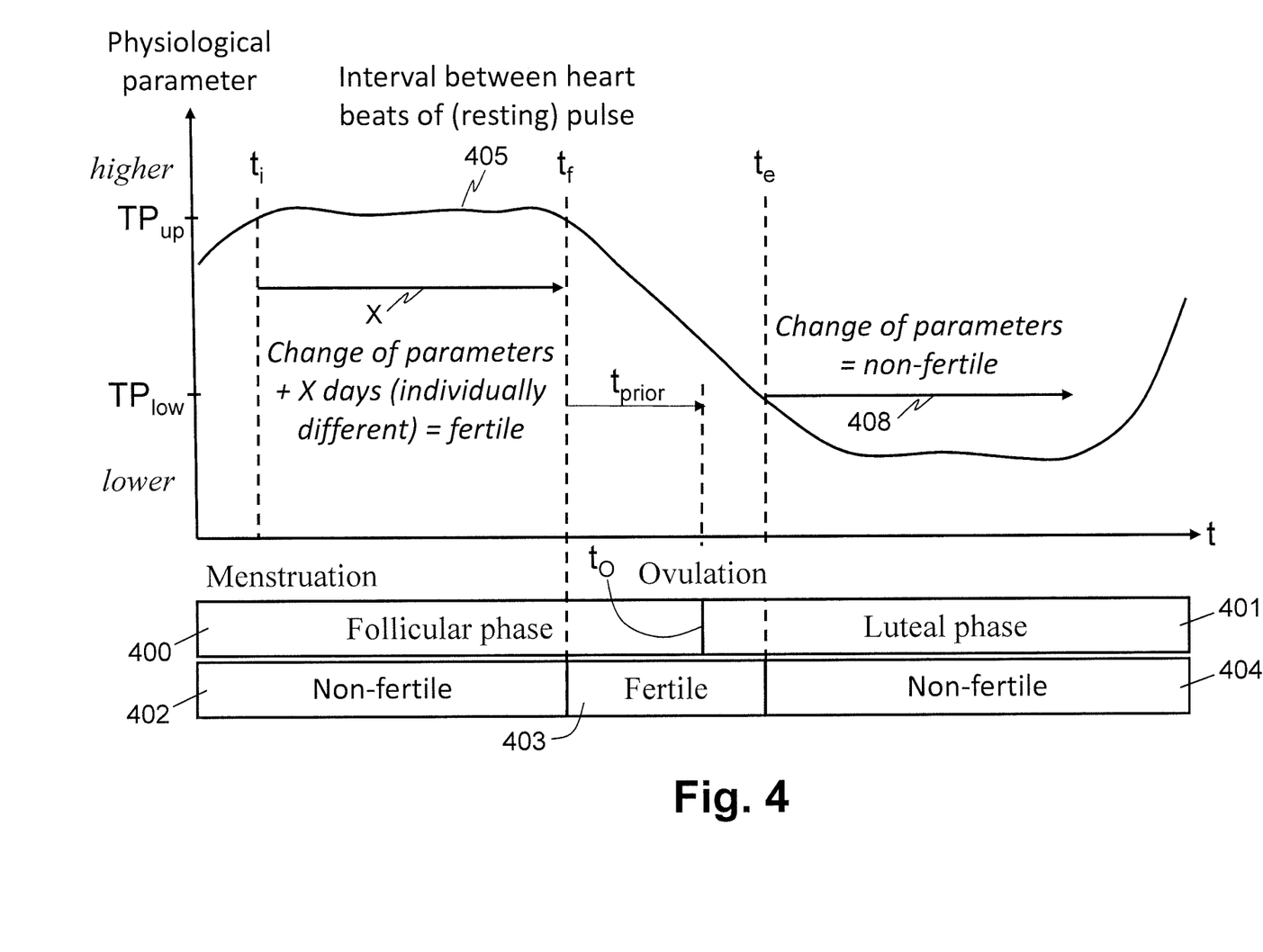
FIG. 4: shows a graph illustrating an example of the temporal change of the interval between heartbeats of the resting pulse.
Figure 5:
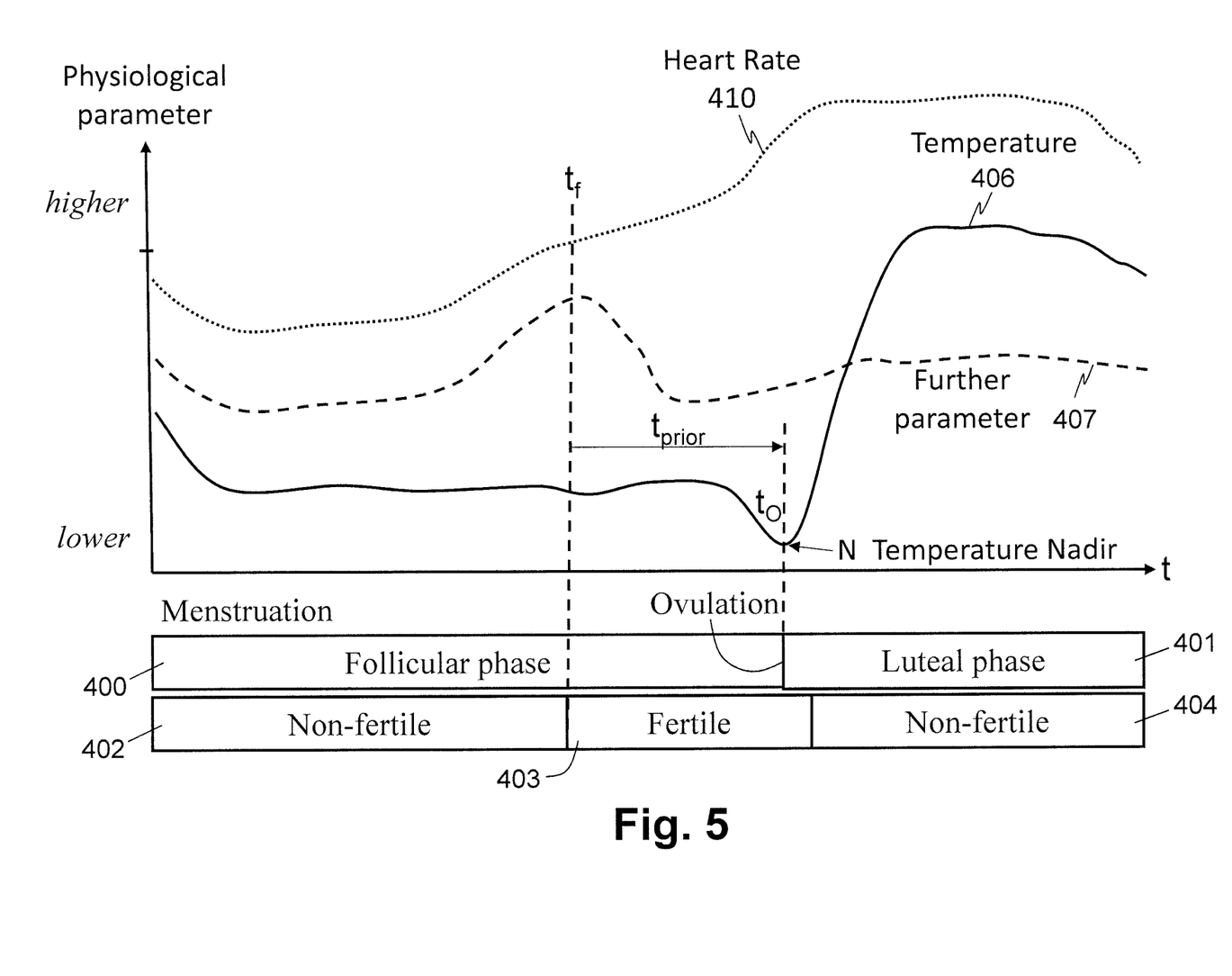
FIG. 5: shows a graph illustrating an example of the temporal change of temperature during the menstrual cycle as well as of the interval between heartbeats of the resting pulse.

As illustrated in FIGS. 4 and 5, the menstrual cycle of a female human includes a follicular phase 400 and a luteal phase 401 which are separated by the time of ovulation $t_O$. As is further illustrated in FIGS. 4 and 5, the fertile phase 403 of the female human begins before and ends after the time of ovulation $t_O$. The beginning of the follicular phase 400 is a non-fertile phase 402; the end of the luteal phase 401 is a non-fertile phase 404.

In the following examples, the functions executed by the processor 13 of the wearable device 1 and/or the processor(s) 30, 40 of the computer system 3 and/or the mobile communication device 4 are described with reference to FIGS. 1a-6. Specifically, described are the functions executed by these processors 13, 30, 40 for determining and indicating the temperature nadir during a menstrual cycle of a female human, as an indicator for the time of ovulation $t_O$ and peak oestrogen level of the female human, and for determining and predicting the starting time of a fertility phase 403 of the female human.

Figure 1A:
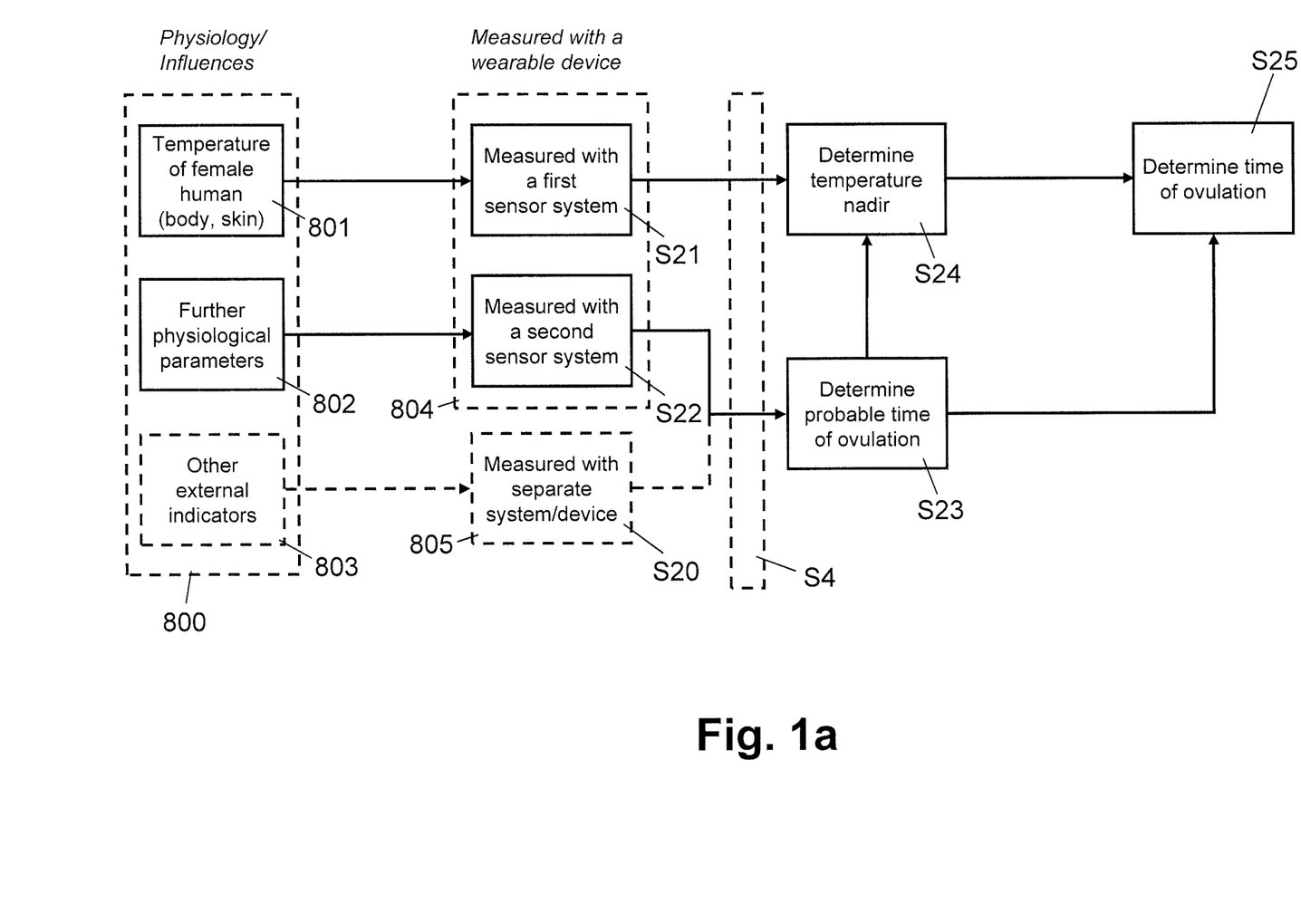
FIG. 1a: shows a flow diagram illustrating schematically an exemplary sequence of steps for determining a time of the temperature nadir during a menstrual cycle of a female, to indicate ovulation and peak oestrogen level of the female human.

In FIG. 1a, box 800 relates to physiological parameters and external indicators, which are taken into consideration for determining the temperature nadir as an indicator for the time of ovulation $t_O$, and peak oestrogen level of the female human. Specifically, the physiological parameters include the body (wrist) and/or skin temperature 801 of the female human (from hereon in short: "body temperature"), and further physiological parameters 802, as measured in steps S1, S2, S3, S10, S11 (see FIGS. 2 and 3), and/or external indicators 803 related to the female human, for determining the starting time $t_f$ of the fertile phase 403 of the female human. For example, the external indicators 803 include results from a urine or saliva test, indicating the presence of an oestrogen metabolite, which is indicative of a fertile phase 403.

In FIG. 1a, box 804 relates to measurements of physiological parameters by way of the wearable device 1. Preferably, the measurements of the various physiological parameters of the female user are performed concurrently. The measurements are performed periodically. In an embodiment, the periodic measurements are limited to specific time intervals, e.g. during nighttime or, more specifically, during the sleep phase with resting pulse.

Specifically, in step S21, a first sensor system of the wearable device 1, the temperature sensor system 104, measures the body temperature 801 of a female user. Specifically, in the state of the device 1 being worn, e.g. on the wrist, the processor 13 of the wearable device 1 reads or receives from the temperature sensor system 104 the currently measured temperature of the female user, specifically the skin temperature but potentially including additional parameters like perfusion, bio-impedance and/or heat loss, e.g. on her wrist. The processor 13 stores the temperature (value) in the data store 12 together with a time stamp, including the current time and date. In step S22, a second sensor system of the wearable device 1 measures further physiological parameters 802 of the female user, as will be described later in more detail. In optional step S20, other systems/devices, separate from the wearable device 1, measure other external indicators 803.

Depending on the embodiment and/or configuration, further processing of the measured body temperature 801 and other physiologic parameters 802 of the female user is performed by the processor 13 of the wearable device 1 and/or by the processor(s) 30, 40 of the computer system 3 and/or the mobile communication device 4. In the case, involving processing by the processor(s) 30 of the computer system 3, the measured and time stamped values of the body temperature 801 and other physiological parameters 802 are transmitted by the communication module 14 from the wearable device 1 via network 2 to the computer system 3, as indicated by step S4 in FIGS. 1a and 2, e.g. directly or via the mobile communication device 4 as a relay device. In the case, involving processing by the processor 40 of the mobile communication device 4, the measured and time stamped values of the body temperature 801 and other physiological parameters 802 are transmitted by the communication module 14 from the wearable device 1 via the close range communication interface to the mobile communication device 4 where they are stored in the data store 41. In the computer system 3 and/or the mobile communication device 4, respectively, the received measurement values are stored securely assigned to the female user, defined, for example, by a user identifier and/or a device identifier (for increased anonymity/privacy). Transmission of the time stamped measurements is performed periodically, for example; typically, the measurement data is transmitted less frequently than the measurements are taken, e.g. various time stamped measurement samples, taken at different times, are grouped and transmitted together by the wearable device 1 in a combined data transmission.

In case other external indicators 803 are measured in optional step S20, the external indicators 803 are entered and stored in the mobile communication device 4 and/or, if applicable, communicated via network 2 to the computer system 3.

In step S23, the processor 13 of the wearable device and/or the processor(s) 30, 40 of the computer system 3 and/or the mobile communication device 4 determine a probable time of ovulation or peak oestrogen level, using the physiological parameters 802 and/or the other external indicators 803 received for the female user. Specifically, the processor(s) 13, 30, 40 determine a time window $w=[t_f \ldots t_w]$ (see FIG. 6) around a probable time $t_p$ when the ovulation or peak oestrogen level is expected to occur. In an embodiment, the processor(s) 13, 30, 40 determine for the time window w a time-probability distribution p1 indicating for various points in time $t_f, t_1, t_2, t_3, t_p, t_4, t_5, t_w$ the probability of the ovulation or peak oestrogen level to occur.

More specifically, the processor(s) 13, 30, 40 determine the probable time $t_p$ when the ovulation or peak oestrogen level is expected to occur based on the starting time $t_f$ of the fertility phase 403 of the female human, by adding a defined user-specific probable time duration $t_{prior}$ to the starting time: $t_p = t_f + t_{prior}$. For example, the user-specific probable time duration $t_{prior}$ is initially a general constant, e.g. 5 days, and is adapted over time based on historic data recorded for the particular individual female user for the time duration between the starting time $t_f$ of the fertility phase 403 and the time of ovulation $t_O$. Different approaches for determining the starting time $t_f$ of the fertility phase 403 will be described later.

In step S24, the processor 13 of the wearable device and/or the processor(s) 30, 40 of the computer system 3 and/or the mobile communication device 4 determine the temperature nadir N (see FIG. 5) in the course of the body temperature 406 recorded for the female user during a menstrual cycle. The core body temperature of an individual tends to have the lowest value in the second half of the sleep cycle. The Basal Body Temperature (BBT) is the body temperature at rest (wake up time). BBT rises after ovulation due to increased progesterone released from the corpus luteum after ovulation. The body temperature nadir N is the point in the menstrual cycle where the core body temperature reaches a minimum before increasing to the higher level in correlation with progesterone in the luteal phase. This typically happens at the day of ovulation in correlation with peak oestrogen level. As is shown in the example of FIG. 5, in the follicular phase 400, the temperature is lower than in the luteal phase 401. As illustrated schematically in FIG. 5 (without proper relative proportion), the temperature nadir N is typically characterized by a temporary decrease in the body temperature 406 of approximately 0.1° C. During the menstrual cycle, the temperature nadir N is indicative of the time of ovulation $t_O$ and peak oestrogen level. However, owing to its relatively small amount of decrease, it could be missed or incorrectly detected in the "noise" of the measurements data. For that reason, the processor(s) 13, 30, 40 determine temperature nadir N further using the probable time $t_p$, the time window w, and/or the time-probability distribution p1 determined in step S23. More specifically, from the temperature 406 recorded for the female user, the processor(s) 13, 30, 40 determine a second probability distribution p2, indicating for the various points in time $t_f, t_1, t_2, t_3, t_p, t_4, t_5, t_w$ of the time window w the probability of the nadir N to occur. The points in time are representative of a sampling period, e.g. one hour, one day or one night, and the probability value for a sampling period indicates the likelihood of the nadir N having occurred in the sampling period, e.g. based on the number of temperature decreases detected in that sampling period.

Figure 6:
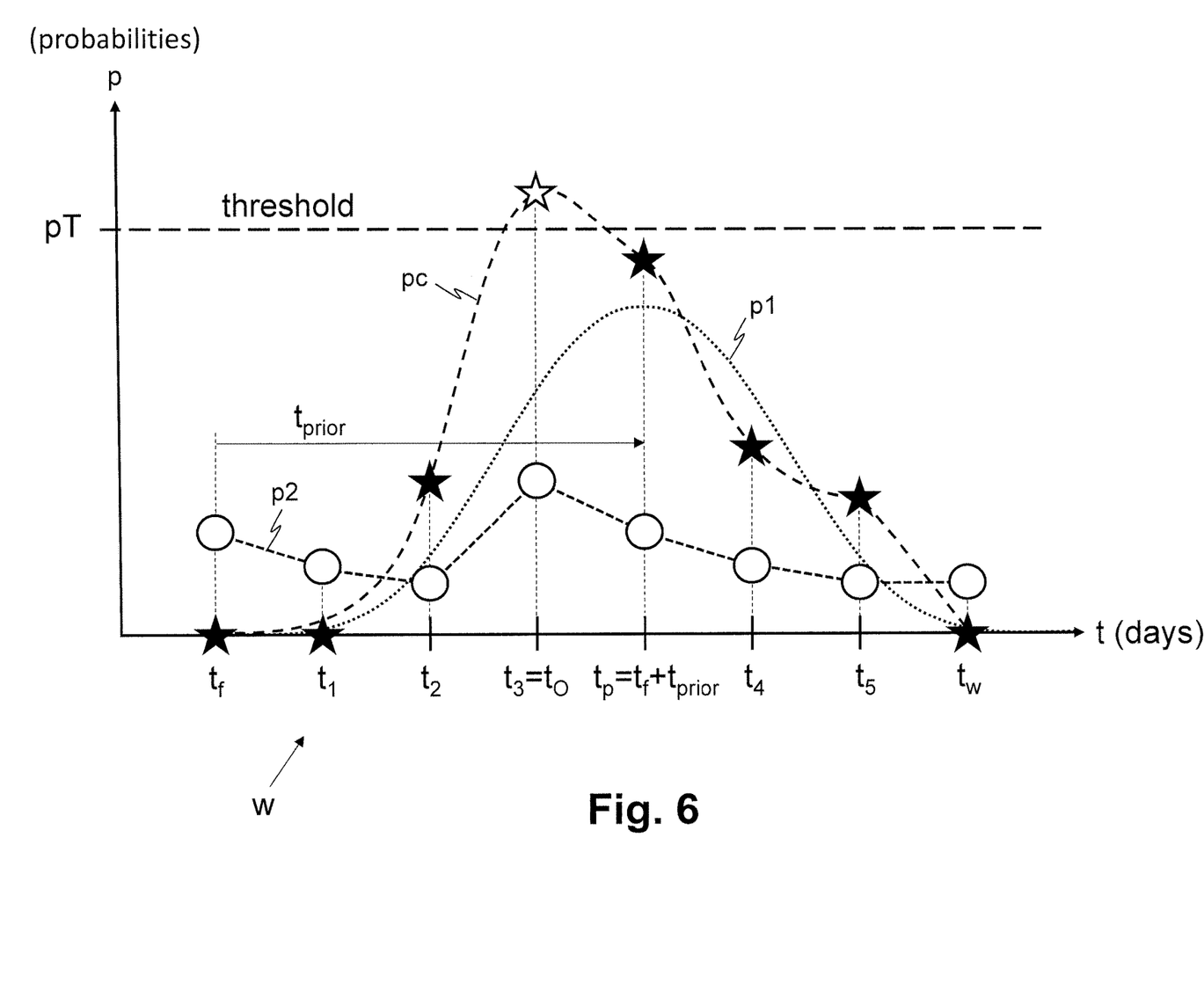
FIG. 6: shows a graph illustrating examples of a first time-probability distribution of ovulation or peak oestrogen level, a second time-probability distribution of the temperature nadir, and a combination of these time-probability distributions used for determining the time of the temperature nadir of a female human.

In an embodiment, using the first and second probability distributions p1, p2, the processor(s) 13, 30, 40 define a combined probability distribution pc, e.g. by multiplying the values of the first and second probability distributions p1, p2. It should be mentioned, that the combined probability distribution pc illustrated in the example of FIG. 6 is scaled or weighted for the illustrative purpose of better clarity and visibility, i.e. it is not depicted with proper numeric proportion. If the processor(s) 13, 30, 40 detect that the combined probability distribution pc exceeds a defined probability threshold pT, the respective point in time $t_3$ is determined to be the time of the temperature nadir N.

In step S25, the processor 13 of the wearable device and/or the processor(s) 30, 40 of the computer system 3 and/or the mobile communication device 4 determine the time of ovulation $t_O$ and/or peak oestrogen level using the time $t_3$ of the temperature nadir N detected in the time window w:$t_O$=$t_3$.

The time of ovulation $t_O$ (and/or peak oestrogen level) is indicated to the user on a user interface of the wearable device 1 or the mobile communication device 4 by the processor 13 or 40, respectively, e.g. as an acoustical signal and/or a graphical representation on the display 16. Depending on the embodiment, the time of ovulation $t_O$ (and/or peak oestrogen level) is transmitted by the processor(s) 30 of the computer system 3 via network 2 to the wearable device 1 and/or the mobile communication device 4.

In the following paragraphs, described with reference to FIGS. 2-5 are different embodiments and configurations for determining and predicting the starting time $t_f$ of the fertility phase 403.

Figure 2:
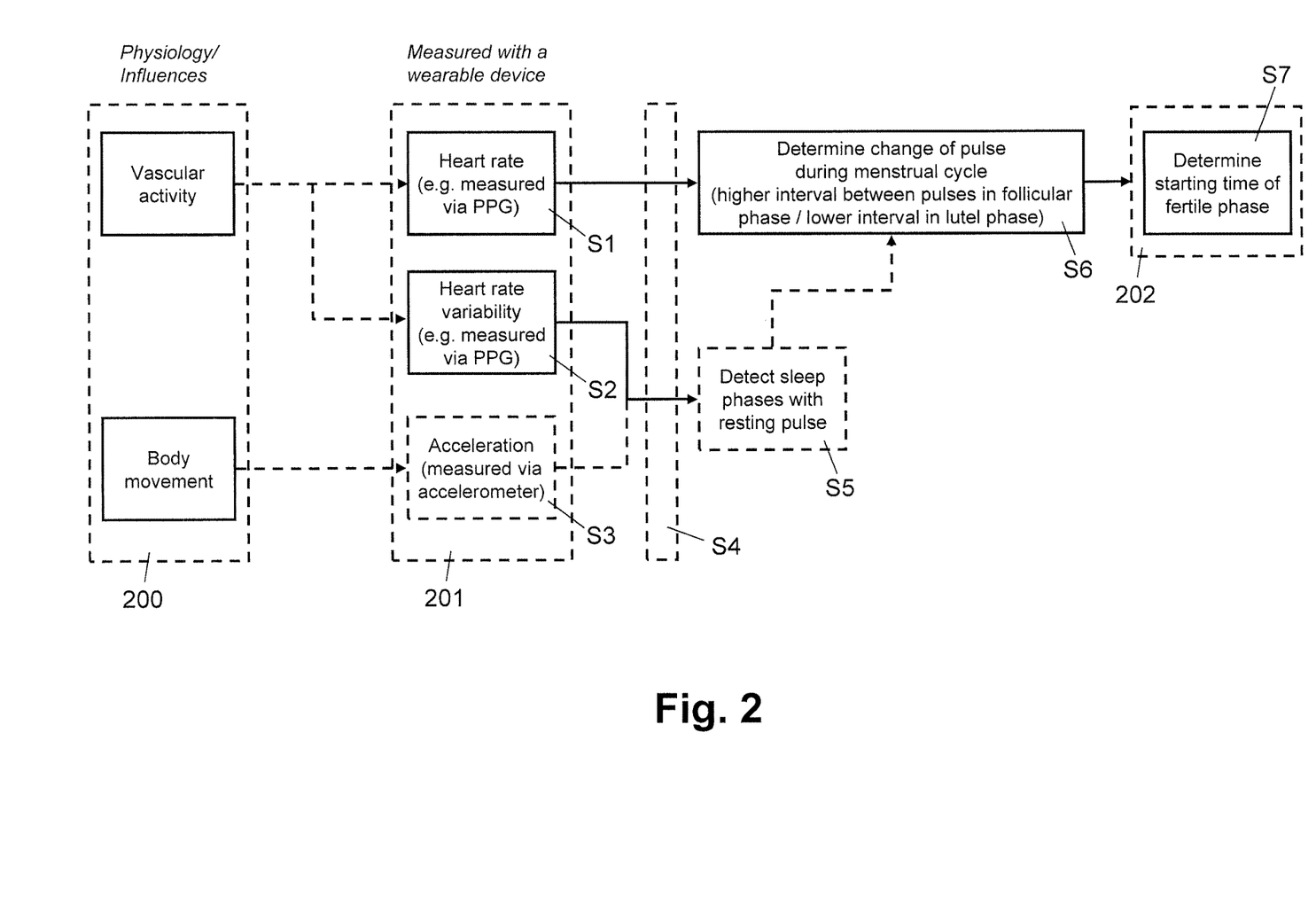
FIG. 2: shows a flow diagram illustrating schematically an exemplary sequence of steps for determining the starting time of a fertility phase of a female human by analyzing the resting pulse during the menstrual cycle.

In FIG. 2, box 200 relates to physiological parameters and other physical influence factors, including vascular activity and body movement of the female user, which are taken into consideration for determining and predicting the starting time $t_f$ of the fertility phase 403.

In FIG. 2, box 201 includes the actual physiological parameters and other indicators that are actually measured for determining and predicting the starting time $t_f$ of the fertility phase 403.

As illustrated in FIG. 2, in step S1, the heart rate of the female user is measured using the wearable device 1. Specifically, in the state of the device 1 being worn, e.g. on the wrist, the processor 13 of the wearable device 1 reads or receives from the sensor system 101 the current heart rate of the female user. The processor 13 stores the heart rate (value) in the data store 12 together with a time stamp, including the current time and date.

In step S2, the heart rate variability of the female user is measured using the wearable device 1. Specifically, in the state of the device 1 being worn, e.g. on the wrist, the processor 13 of the wearable device 1 reads or receives from the sensor system 101 the current heart rate variability of the female user. The processor 13 stores the heart rate variability (value) in the data store 12 together with a time stamp, including the current time and date.

In step S3, the movement or acceleration, respectively, of the female user is measured using the wearable device 1. Specifically, in the state of the device 1 being worn, e.g. on the wrist, the processor 13 of the wearable device 1 reads or receives from the sensor system 102 the current acceleration of the female user, e.g. the current acceleration of her wrist. The processor 13 stores the acceleration (value) in the data store 12 together with a time stamp, including the current time and date. As will be explained later, in some simplified embodiments, step S3 is omitted, as the starting time t of the fertility phase 403 is determined without using user acceleration.

As mentioned above, the measurements of the physiological parameters are performed periodically, for example, the sensor system 101 uses the optical sensors to measure the heart rate and heart rate variability every couple of milliseconds.

Further processing of the measured physiologic parameters, including heart rate, heart rate variability, and acceleration of the female user, is performed by the processor 13 of the wearable device and/or by the processor(s) 30, 40 of the computer system 3 and/or the mobile communication device 4, as described above in connection with FIG. 1a. In the latter case, the measured and time stamped heart rate, heart rate variability, and acceleration are transmitted from the wearable device 1 via network 2 to the computer system 3 where they are stored securely assigned to the female user and/or her device, respectively, as indicated by step S4.

In step S5, multiple physiological parameters, including the heart rate variability and the acceleration, are used (by the processor 13 of the wearable device and/or by the processor(s) 30, 40 of the computer system 3 and/or the mobile communication device 4) to detect sleep phases with a resting pulse. Detecting sleep phases with resting pulse makes it possible to detect the pulse each night during the menstrual cycle in the same state of activity and arousal of the female user. The sleep phases are detected, for example, by combining the measurements of the heart rate variability and acceleration as described by Renevey et al. cited above. In a simplified embodiment, the sleep phase is determined without using user acceleration, for example based on a user-defined sleep interval, e.g. between 3:00 am and 4:00 am.

In step S6, the processor 13 of the wearable device and/or the processor(s) 30, 40 of the computer system 3 and/or the mobile communication device 4 detect changes of the pulse, e.g. the resting pulse, during the menstrual cycle of the female user. In other words, the processor(s) 13, 30, 40 determine changes of the heart rate, i.e. changes in the duration of the interval between individual heartbeats, respectively, that occur during the detected sleep phases with resting pulse. Specifically, the processor(s) 13, 30, 40 determine the points in time when the resting pulse changes from short to long intervals in the early follicular phase 400 and when the resting pulse changes from long to short intervals at the beginning of the fertile phase and in the luteal phase 401. Typically, the changes in the duration of the beat to beat intervals vary between 35 ms and 105 ms. For example, the Deep Sleep (or Slow Wave Sleep) phase is considered a sleep phases with resting pulse. In a simplified embodiment, the wearable device 1 and/or the processor(s) 30, 40 of the computer system 3 and/or the mobile communication device 4 detect changes of the pulse during the menstrual cycle of the female, without a limitation to a detected sleep phase, but at a specific point in time, e.g. during the night, for example based on a user-defined sleep interval, e.g. between 3:00 am and 4:00 am.

In FIG. 4, reference numeral 405 refers to the graph that shows the change of the interval between heartbeats during the menstrual cycle. As is shown in the example of FIG. 4, in the follicular phase 400, the duration of the interval between heartbeats is longer than the duration of the intervals between pulses in the luteal phase 401. The change of the resting pulse (from short to long intervals) in the follicular phase 400 is indicated by time $t_i$ when the duration of the interval between individual pulses exceeds a defined upper threshold $TP_{up}$. The change of the resting pulse (from long to short intervals) in the luteal phase 401 is indicated by time $t_e$ when the duration of the interval between individual pulses is below a defined lower threshold $TP_{low}$. The values of the upper and lower thresholds $TP_{up}$ and $TP_{low}$ are determined individually for the female user by the processor 13 of the wearable device and/or the processor(s) 30, 40 of the computer system 3 and/or the mobile communication device 4. The values of the upper and lower thresholds $TP_{up}$ and $TP_{low}$ are determined as a defined percentage p, q (for example p>90%, e.g. p=97%; q<110%, e.g. q=102%) of the maximum $PI_{max}$ and minimum levels of the intervals between the heartbeats recorded on average for the particular female users during a plurality n of menstrual cycles $$TP_{up} = p \cdot \left(\frac{1}{n}\sum_n PI_{max_n}\right) \text{ and } TP_{low} = q \cdot \left(\frac{1}{n}\sum_n PI_{min_n}\right),$$

respectively.

In FIG. 2, block 202 refers to processing steps performed, by the processor 13 of the wearable device and/or the processor(s) 30, 40 of the computer system 3 and/or the mobile communication device 4, using the detected changes of the resting pulse.

In step S7, the processor(s) 13, 30, 40 calculate the starting time $t_f$ of the fertile phase 403 in the menstrual cycle of the female user based on the detected changes of the resting pulse. As illustrated in FIG. 4, the starting time $t_f$ of the fertile phase 403 can be determined, based on a detected end point of the period of pulses with the comparatively long interval between heartbeats, e.g. at the point in time $t_f$ when the duration of the interval between individual pulses falls again below the defined upper threshold $TP_{up}$ or another defined threshold value. In a second approach illustrated in FIG. 4, the starting time t of the fertile phase 403 is calculated, based on the point in time $t_i$ when the duration of the interval between individual pulses exceeds a defined upper threshold $TP_{up}$, by adding a defined user-specific time duration X to that time of change: $t_f = t_i + X$. The starting-time-based approach ($t_i + X$) can be executed as an alternative to the end-point-based approach ($t_f$) for calculating the starting time $t_f$ of the fertile phase 403, or in combination with the starting-time-based approach ($t_i + X$), e.g. by calculating an average value from the results of the two approaches.

As further illustrated in FIG. 4, the ending time $t_e$ of the fertile phase 403 is defined based on the point in time $t_e$ when the duration of the interval between individual pulses is below the defined lower threshold $TP_{low}$.

For example, the user-specific time duration X is calculated as a defined percentage r (for example 50%≤r≤70%, e.g. r=60%) of the duration between the point in time $t_i$ when the duration of the interval between individual pulses exceeds the defined upper threshold $TP_{up}$ and the point in time $t_e$ when the duration of the interval between individual pulses is below a defined lower threshold $TP_{low}$, determined on average for the particular female user during a plurality n of menstrual cycles $$X = r \cdot \left(\frac{1}{n}\sum_n (t_{f_n} - t_{i_n})\right).$$

As will be described later, in further embodiments, additional physiological parameters and indicators are used to refine the timing of the fertility phase 403 or the user-specific time duration X, respectively.

Figure 3:
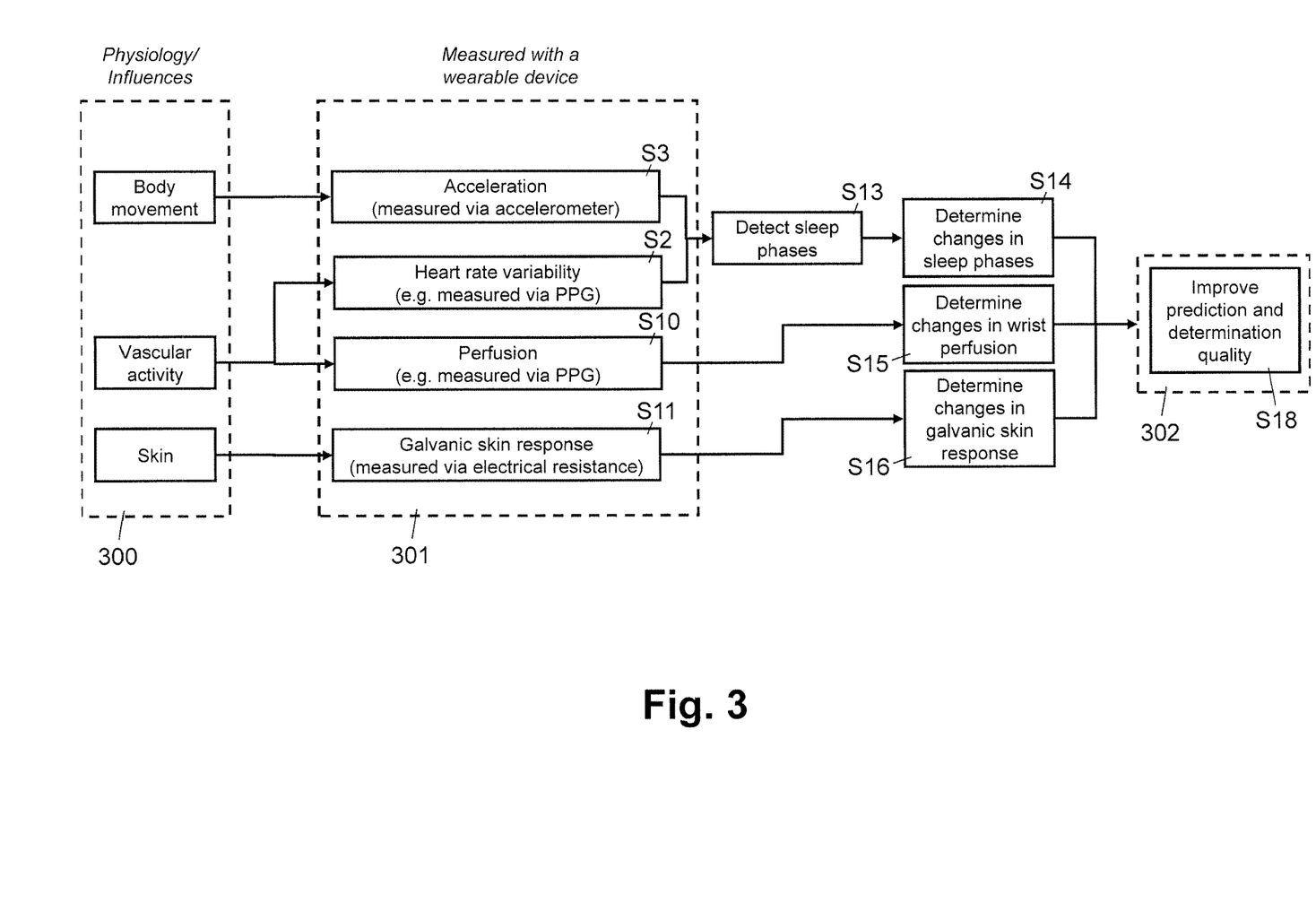
FIG. 3: shows a flow diagram illustrating schematically an exemplary sequence of steps for improving the prediction and determination of the starting time of a fertility phase of a female human by analyzing further physiological parameters during the menstrual cycle.

In FIG. 3, box 300 relates to an extended set of physiological parameters and other physical influence factors, which are taken into consideration for determining and predicting the starting time t of the fertility phase 403.

In FIG. 3, box 301 includes an extended set of further physiological parameters and other indicators that are actually measured for determining and predicting the starting time t of the fertility phase 403.

As illustrated in FIG. 3, in step S10, the perfusion of the female user, e.g. the wrist perfusion, is measured using the wearable device 1. Specifically, in the state of the device 1 being worn, e.g. on the wrist, the processor 13 of the wearable device 1 reads or receives from the sensor system 101 the current (wrist) perfusion of the female user. The processor 13 stores the perfusion (value) in the data store 12 together with a time stamp, including the current time and date.

In step S11, the galvanic skin response of the female user's, e.g. on her wrist, is measured using the wearable device 1. Specifically, in the state of the device 1 being worn, e.g. on the wrist, the processor 13 of the wearable device 1 reads or receives from the galvanic skin response sensor system 103 the current electrical resistance or conductance of the skin of the female user's, e.g. of the wrist. The processor 13 stores the galvanic skin response (value) in the data store 12 together with a time stamp, including the current time and date.

Preferably, the measurements of the heart rate, heart rate variability, perfusion, acceleration, temperature, and galvanic skin response of the female user are performed concurrently. The measurements are performed periodically, e.g. once or more every second. In an embodiment, the periodic measurements are limited to specific time intervals, e.g. during nighttime or, more specifically, during the sleep phase with resting pulse.

As described above in the context of FIG. 1a, depending on the embodiment and/or configuration, further processing of the measured parameters and indicators is performed by the processor 13 of the wearable device, the processor 40 of the mobile communication device 4, and/or by the processor(s) 30 of the computer system 3. In the latter case, the measured and time stamped parameters and indicators are transmitted from the wearable device 1 via network 2 to the computer system 3 where they are stored securely assigned to the female user and/or her device, respectively.

In step S13, the heart rate variability and the acceleration are used by the processor(s) 13, 30 to detect different sleep phases, e.g. by combining the measurements of the heart rate variability and acceleration as described by Renevey et al. cited above.

In step S14, the processor(s) 13, 30, 40 detect changes of the sleep phases during the menstrual cycle of the female user.

In step S15, the processor(s) 13, 30, 40 detect changes of the perfusion during the menstrual cycle of the female user.

In step S16, the processor(s) 13, 30, 40 detect changes of the galvanic skin response during the menstrual cycle of the female user.

In step S17, the processor(s) 13, 30, 40 detect changes of the measured body or wrist temperature during the menstrual cycle of the female user. Typically, the changes vary between 0.24° C.-0.5° C.

It should be pointed out, that the changes of the resting pulse, the sleep phases, the perfusion, and the galvanic skin response, and the temperature are detected in steps S6, S14, S15, and S16, respectively, for measurements recorded during the current menstrual cycle with respect to their dynamic (temporal) change in the course of the current menstrual cycle and/or with respect to measurements recorded for previous menstrual cycles of the female user. A specific dynamic change of a parameter is detected by comparing the measurements of the particular parameter to defined thresholds and identifying the change or its point in time, respectively, when the parameter exceeds or is below the particular threshold. A change of a parameter with regards to measurements recorded in previous menstrual cycles is detected by comparing the measurements of the particular parameter to thresholds that are defined depending on measurements recorded in previous menstrual cycles.

In FIG. 3, block 302 refers to processing steps performed by the processor(s) 13, 30, 40 to improve accuracy and quality of determining the starting time $t_f$ of the fertile phase 403 of the female user based on the parameters and indicators determined in steps S2, S3, S10, S11, and S13, and processed in steps S14, S15, and S16. Specifically, the processor(s) 13, 30, 40 are configured to detect correlations among the measured physiological parameters and external indicators, and to determine the detected starting point $t_f$ of the fertility phase 403, using the (correlation) time of the detected correlations.

In an embodiment, the processor(s) 13, 30, 40 are configured to determine the detected starting point $t_f$ of the fertility phase 403, using a detected time of increased heart rate variability, e.g. as described in WO 2015/150434.

In an embodiment, the processors 30 of the cloud-based computer system 3 are configured to implement an online user platform. The online user platform is configured to provide to authorized users secured access to their private personal data and stored measurement data.

It should be noted that, in the description, the computer program code has been associated with specific functional modules and the sequence of the steps has been presented in a specific order, one skilled in the art will understand, however, that the computer program code may be structured differently and that the order of at least some of the steps could be altered, without deviating from the scope of the invention.

The invention claimed is:

1. An electronic system for determining a temperature nadir during a menstrual cycle of a female human, the system comprising:
 a wearable device including a first sensor system configured to be worn in contact with skin of the female human and to determine a temperature of the female human, and
 a processor configured to receive the temperature of the female human from the first sensor system and one or more further measured physiological parameters of the female human in a current menstrual cycle, wherein the one or more further measured physiological parameters of the female human comprise at least one of: heart rate or heart rate variability;
 the processor being further configured to determine a detected starting point of a fertility phase of the female human in the current menstrual cycle based at least in part on a change in the one or more further measured physiological parameters of the female human, wherein the detected starting point of the fertility phase is determined based on:
 (i) a defined length of time after a duration of an interval between pulses of the heart rate exceeds a defined threshold value during the current menstrual cycle, or
 (ii) when the duration of the interval between pulses of the heart rate drops below the defined threshold value after the duration of the interval between pulses of the heart rate previously exceeded the defined threshold value during the current menstrual cycle; and
 the processor being further configured to, after the detected starting point of the fertility phase, detect the temperature nadir as a temporary decrease in the temperature received from the first sensor system, wherein the processor is configured to detect the temperature nadir in a time window after the detected starting point of the fertility phase of the female human in the current menstrual cycle, a time of the temperature nadir being indicative of time of ovulation and peak oestrogen level.

2. The electronic system of claim 1, wherein the processor is configured to determine the nadir of the temperature by detecting the temporary decrease of the temperature within a time window around a probable time when the ovulation or peak oestrogen level is expected to occur, the probable time being based on the detected starting point of the fertility phase of the female human.

3. The electronic system of claim 2, wherein the processor is configured to determine the probable time when the ovulation or peak oestrogen level is expected to occur as a first time-probability distribution, indicating for various points in time of the time window the probability of the ovulation or peak oestrogen level to occur, and to determine a second time-probability distribution, indicating for various points in time of the time window the probability of the nadir of the temperature to occur, by detecting the temporary decrease of the temperature, and to determine the time of the temperature nadir by comparing a combination of the first time-probability distribution and the second time-probability distribution to a threshold.

4. The electronic system of claim 2, wherein the processor is configured to determine the probable time when the ovulation or peak oestrogen level is expected to occur by adding a probable time duration to the detected starting point of the fertility phase.

5. The electronic system of claim 2, wherein the electronic system further comprises a data store, and the processor is configured to store in the data store at least one of: one or more further physiological parameters measured by a second sensor system, included in the wearable device and configured to be worn in contact with the skin of the female human, and other external indicators related to the female human, and to determine the probable time when the ovulation or peak oestrogen level is expected to occur, using the one or more further physiological parameters and other external indicators of the female human stored during a plurality of menstrual cycles.

6. The electronic system of claim 1, wherein the wearable device includes a second sensor system configured to be worn in contact with the skin of the female human and to determine a heart rate of the female human; and the processor is configured to determine a change in pulse during a menstrual cycle using the heart rate, and wherein the determination of the detected starting point of the fertility phase is based at least in part on the change in the pulse.

7. The electronic system of claim 6, wherein the processor is configured to determine the detected starting point of the fertility phase using the time ($t_1$) of the change of the pulse from a comparatively short interval between heartbeats to a comparatively longer interval between heartbeats.

8. The electronic system of claim 6, wherein the processor is configured to determine the detected starting point of the fertility phase by detecting a time indicative of an end point of a period of pulses with a comparatively long interval between heartbeats.

9. The electronic system of claim 1, wherein the wearable device includes a second sensor system configured to be worn in contact with the skin of the female human and to determine a heart rate variability of the female human; and the processor is configured to determine the detected starting point of the fertility phase, using a time of increased heart rate variability.

10. The electronic system of claim 9, wherein the second sensor system is configured to determine acceleration of the female human; and the processor is configured to detect during menstrual cycles sleep phases with resting pulse using the heart rate variability and the acceleration, to determine a change in the resting pulse during a menstrual cycle using the heart rate, and to determine the detected starting point of the fertility phase, using a time of the change in the resting pulse.

11. The electronic system of claim 1, wherein the wearable device includes a second sensor system configured to be worn in contact with the skin of the female human and to determine one or more further physiological parameters of the female human; and the processor is configured to determine correlations of at least one of: the one or more further physiological parameters measured by the second sensor system and other external indicators related to the female human, and to determine the detected starting point of the fertility phase, using a correlation time of the correlations of the one or more further physiological parameters and other external indicators.

12. The electronic system of claim 1, wherein the processor is arranged in the wearable device and configured to determine the time of the temperature nadir using physiological parameters measured by the sensor systems of the wearable device.

13. The electronic system of claim 1, wherein the processor is arranged in an external system, separated from the wearable device, the wearable device further comprises a communication module configured to transmit physiological parameters measured by the sensor systems of the wearable device to the external system, and the processor is configured to determine the time of the temperature nadir using the physiological parameters received from the wearable device.

14. A method of determining a temperature nadir during a menstrual cycle of a female human, the method comprising:
receiving in a processor from a first sensor system of a wearable device a temperature of the female human;
receiving in the processor one or more further measured physiological parameters of the female human in a current menstrual cycle, wherein the one or more further measured physiological parameters of the female human comprise at least one of: heart rate or heart rate variability;
determining by the processor a detected starting point of a fertility phase of the female human in the current menstrual cycle based at least in part on a change in the one or more further measured physiological parameters of the female human, wherein the detected starting point of the fertility phase is determined based on:
(i) a defined length of time after a duration of an interval between pulses of the heart rate exceeds a defined threshold value during the current menstrual cycle, or
(ii) when the duration of the interval between pulses of the heart rate drops below the defined threshold value after the duration of the interval between pulses of the heart rate previously exceeded the defined threshold value during the current menstrual cycle; and
after the detected starting point of the fertility phase, detecting by the processor the temperature nadir as a temporary decrease in the temperature received from the first sensor system, wherein the temperature nadir is detected in a time window after the detected starting point of the fertility phase of the female human in the current menstrual cycle, a time of the temperature nadir being indicative of time of ovulation and peak oestrogen level.

15. The method of claim 14, wherein the method further comprises determining by the processor a probable time when the ovulation or peak oestrogen level is expected to occur as a first time-probability distribution, indicating for various points in time of the time window the probability of the ovulation or peak oestrogen level to occur; and determining by the processor a second time-probability distribution, indicating for various points in time of the time window the probability of the nadir of the temperature to occur, by detecting the temporary decrease of the temperature; and determining by the processor the time of the temperature nadir by comparing a combination of the first time-probability distribution and the second time-probability distribution to a threshold.

16. A computer program product comprising a non-transient computer readable medium having stored thereon computer program code configured to control one or more processors of a computerized system, such that the computerized system performs the steps of:
receiving from a first sensor system of a wearable device a temperature of a female human;
receiving one or more further measured physiological parameters of the female human in a current menstrual cycle, wherein the one or more further measured physiological parameters of the female human comprise at least one of: heart rate or heart rate variability;
determining a detected starting point of a fertility phase of the female human in the current menstrual cycle based at least in part on a change in the one or more further measured physiological parameters of the female human, wherein the detected starting point of the fertility phase is determined based on:
(i) a defined length of time after a duration of an interval between pulses of the heart rate exceeds a defined threshold value during the current menstrual cycle, or
(ii) when the duration of the interval between pulses of the heart rate drops below the defined threshold value after the duration of the interval between pulses of the heart rate previously exceeded the defined threshold value during the current menstrual cycle; and
after the detected starting point of the fertility phase, detecting a temperature nadir as a temporary decrease in the temperature received from the first sensor system wherein the temperature nadir is detected in a time window after the detected starting point of the fertility phase of the female human in the current menstrual cycle, a time of the temperature nadir being indicative of time of ovulation and peak oestrogen level.

* * * * *